United States Patent [19]

Rader et al.

[11] 4,436,942

[45] Mar. 13, 1984

[54] PROCESS FOR THE CATALYZED FLUORINATION OF HALOALKYL AROMATIC COMPOUNDS

[75] Inventors: Charles G. Rader, Grand Island; Stephen Robota, North Tonawanda, both of N.Y.

[73] Assignee: Occidental Chemical Corporation, Niagara Falls, N.Y.

[21] Appl. No.: 34,803

[22] Filed: Apr. 30, 1979

Related U.S. Application Data

[63] Continuation of Ser. No. 846,047, Oct. 27, 1977, abandoned.

[51] Int. Cl.³ .................................................. C07C 9/08
[52] U.S. Cl. ..................................................... 570/145
[58] Field of Search ........................... 260/651 F, 650 F; 570/145

[56] References Cited

U.S. PATENT DOCUMENTS

| | | | |
|---|---|---|---|
| 2,946,828 | 7/1960 | Scherer et al. | 260/653.7 |
| 3,258,500 | 6/1966 | Sautemer et al. | 260/651 F |
| 3,755,477 | 8/1973 | Firth et al. | 260/651 F |
| 3,836,479 | 9/1974 | Pauksch et al. | 260/653.7 |
| 3,859,372 | 1/1975 | Robota | 260/651 F |
| 3,966,832 | 6/1976 | Lademann et al. | 260/651 F |
| 4,045,502 | 8/1977 | Bhutani et al. | 260/651 F |
| 4,242,286 | 12/1980 | Ohsaka | 570/145 |

FOREIGN PATENT DOCUMENTS 1155104 10/1963 Fed. Rep. of Germany ... 260/653.7

*Primary Examiner*—Curtis R. Davis
*Attorney, Agent, or Firm*—J. F. Tao; A. S. Cookfair; W. G. Gosz

[57] ABSTRACT

A process for the preparation of compounds of the formula

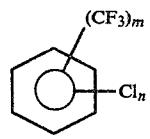

which comprises contacting compounds of the formula

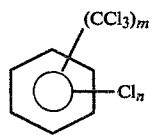

wherein
n is 0 to 5, and
m is 1 to 3 in the vapor phase, with hydrogen fluoride in the presence of a granular, porous high surface area catalyst prepared by treating α-alumina with hydrogen fluoride.

19 Claims, No Drawings

# PROCESS FOR THE CATALYZED FLUORINATION OF HALOALKYL AROMATIC COMPOUNDS

This is a continuation of application Ser. No. 846,047, filed Oct. 27, 1977, and now abandoned.

BACKGROUND OF THE INVENTION

This invention relates to a process for the preparation of fluoromethyl aromatic compounds, and, in particular, to a process for the catalyzed vapor phase replacement of halogen atoms of halomethyl aromatic compounds with fluorine atoms.

Various fluorination processes are known wherein fluorine replaces substituents of organic compounds, such as halogen atoms. Known processes of this type include both vapor phase fluorination reactions and liquid phase fluorination reactions. Typically, such processes involve the reaction of an organic halide with a fluorinating agent, such as hydrogen fluoride, sometimes in the presence of a catalyst, at atmospheric or super-atmospheric pressures. However, many of the known processes, while suitable for laboratory investigations and experiments, or small scale preparations, are unsuitable for larger scale commercial use for various reasons, such as the low purity of product obtained as well as the high cost of equipment employed. In addition, many of the known commercial fluorination processes employ catalysts which, although useful in obtaining an increase in efficiency of the fluorination reaction, present difficulties such as the frequent need for replacement due to loss, deactivation or physical deterioration of the catalyst. For example, one of the common difficulties encountered in vapor phase fluorination reactions results from the highly exothermic nature of such reactions. The heat evolved frequently results in a temperature rise sufficient to cause thermal decomposition of some of the organic materials present with a resultant carbonization of the catalyst. In other instances, materials that provide good catalytic activity for a given reaction under laboratory conditions are too costly or lack the physical stability desirable for use as a catalyst under the rigorous requirements of a continuous commercial process.

A wide variety of fluorination catalysts are known and have been used for various fluorination processes. However, the efficacy of a particular catalyst is highly specific and may depend on the nature of the reactants, that is, the specific compound to be fluorinated and the particular fluorinating agent employed as well as the condition of the fluorination reaction, such as temperature, pressure, and physical phase of reactants.

It is an object of this invention to provide an improved process for the catalyzed vapor phase fluorination of chloromethyl aromatic compounds. It is a further object to provide such process utilizing an improved catalyst therefore that is highly effective, relatively low in cost, and stable under conditions of vapor phase fluorination of chloromethyl aromatic compounds. It is a still further object to provide an improved vapor phase process for the production of trifluoromethyl aromatic compounds.

SUMMARY OF THE INVENTION

In accordance with this invention there is provided a novel process for the preparation of a compound of the formula

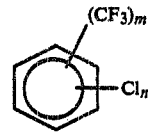

which comprises contacting a compound of the formula

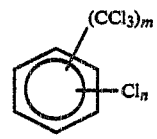

wherein
n is 0 to 5, and
m is 1 to 3
in the vapor phase, with hydrogen fluoride in the presence of a catalyst prepared by treating α-alumina with hydrogen fluoride.

The treated alumina catalyst employed in the process of this invention is prepared by the reaction of hydrogen fluoride with γ-alumina. The γ-alumina is one of the crystalline modifications of alumina, which may be prepared by thermal decomposition of alumina hydrates. Details regarding the structure and methods of preparation of crystalline alumina, including γ-alumina are known in the literature and disclosed for example in structure of metallic catalysts, Academic Press, 1975, pages 46–54. Gamma-alumina is commercially available in various forms, sizes and shapes. To prepare the prefluorinated catalysts, useful in the process of this invention, it is preferred to employ as the starting material, particulate γ-alumina having a surface area of about 50 to about 800 and preferably about 50 to about 400 meters pre gram and a particle size preferably in the range of about 0.2 to about 2 cm. average diameter. The prefluorination of the γ-alumina is accomplished by reaction of hydrogen fluoride with the γ-alumina, preferably at a temperature of about 200° to about 600° Celsius. Typically, such pre-fluorination may be carried out by passing hydrogen fluoride, optionally in admixture with an inert diluent gas, such as nitrogen, through a column or packed bed or fluidized bed of the γ-alumina particles. Alternatively, the pre-fluorination may be effected in-situ in the organic reaction vessel prior to introduction of the organic reactant. The reaction, which is exothermic, is typically continued until the reaction exotherm ceases or substantially declines. In the preparation of the catalyst, the pre-fluorination of the γ-alumina will result in a decrease of surface area (as measured by standard B.E.T. nitrogen adsorption techniques). Pre-fluorination of γ-alumina in the manner described will typically result in the formation of a pre-fluorinated catalyst having a surface area of about 4 to about 40 square meters per gram, and a fluorine content of about 20 to about 62 weight percent.

The fluorinated γ-alumina, thus prepared, has been found highly effective for the vapor phase fluorination of benzotrichloride compounds with the replacement of chlorine atoms on the side chain by fluorine atoms without substantial effect on any nuclear halogen atoms present. In addition, it is a particular advantage that through the use of such catalyst in the process of this invention the trichloromethyl groups of the benzotrichloride can readily be fully fluorinated resulting in substantially complete conversion to trifluoromethyl groups.

The benzotrichlorides which can be efficiently fluorinated in accordance with this invention are benzotrichlorides and nuclear chlorinated benzotrichlorides, including, for example trichloromethylbenzene (benzotrichloride), monochloro-trichloromethyl benzene (e.g. o-, m-, and p-chlorobenzotrichloride), dichloro-trichloromethylbenzene, trichloro-trichloromethylbenzene, di-(trichloromethyl) benzene monochloro-di-(trichloromethyl) benzene and the like. In a preferred embodiment, the present invention is directed to the fluorination of benzotrichloride and p-chlorobenzotrichloride.

The process of this invention is typically carried out by passing the benzotrichloride vapors, together with gaseous HF, through a packed bed of particulate, pre-fluorinated, $\gamma$-alumina, preferably maintained at a temperature of about 100° to about 600° and most preferably about 250° to about 450° Celsius. Hydrogen fluoride is preferably employed in excess of the stoichiometric amount required for conversion of all the trichloromethyl groups to trifluoromethyl groups. It is preferred to employ an excess of the hydrogen fluoride of about 10% to about 80% of the stoichiometric amount.

It is preferred to carry out the fluorination process at atmospheric pressures. However, sub-atmospheric or super-atmospheric pressures may be employed, if desired.

The flow rate or retention time of the reactants through the bed of $\gamma$-alumina may vary considerably, depending on the volume of reactants and volume of catalyst bed. Generally, the amount of catalyst to be used is a function of the desired production rate and retention time of the process. Thus, in the present invention as related to vapor phase work, an amount of catalyst, which will give nominal retention times of from 0.5 to about 60 seconds, and preferably at from 5 to about 25 seconds, is employed, resulting in satisfactory performance. Typically, conversions obtained with representative compounds have been as high as 98 percent and yields have been greater than 90 percent.

It is a particular advantage in the process of this invention that the pre-fluorinated $\gamma$-alumina catalyst exhibits a high degree of physical stability and as a result may be periodically regenerated to remove carbonaceous material from the surface without substantial physical deterioration. In practice, the need for catalyst regeneration is indicated by a decrease in fluorination efficiency as evidenced by an increase in non-fully fluorinated substituents in the reaction product. The regeneration of the catalyst may be effected by passing air or oxygen through the catalyst bed at an elevated temperature, preferably about 200° to about 650° Celsius. The regeneration is an exothermic reaction. Substantial completion of the regeneration is indicated by a decrease in the exotherm, with a resultant lowering of temperature, caused by removal of carbonaceous material from the catalyst surface. Following such regeneration, the catalyst is again pre-fluorinated as described hereinabove, prior to use in the process of the invention.

In the above-described processes of pre-fluorination, fluorination of the organic material, and regeneration of the catalyst, it is important that the temperature of such reactions or treatments be maintained at below about 650° Celsius. At temperatures above about 650° Celsius, phase transformations of the catalyst are likely to occur, resulting in the formation of other crystalline modifications, including the formation of $\gamma$-alumina type crystalline phase, which has been found to be substantially less efficient in the catalysis of the fluorination of aromatic trichloromethyl compounds.

The following specific examples are provided to further illustrate this invention and the manner in which it may be carried out. It will be understood that the specific details given in the examples have been chosen for purpose of illustration and are not to be construed as a limitation of the invention. In the examples, unless otherwise indicated, all parts and percentages are by weight and all temperatures are in degrees Celsius.

EXAMPLE 1

A pre-fluorinated $\gamma$-alumina catalyst was prepared from 851 parts of spheres of $\gamma$-alumina having an average diameter of about 0.6 cm. and a surface area of about 335 m$^2$/g. Initially, a bed of the $\gamma$-alumina spheres packed in a tubular reactor was heated to about 110° C. and maintained at about that temperature for about one half hour while a stream of nitrogen was passed therethrough from the bottom of the reactor. Hydrogen fluoride was then passed through the bed together with the nitrogen. The contact of the $\gamma$-alumina and hydrogen fluoride resulted in an exotherm and the temperature of the bed rose quickly to about 200° C. Hydrogen fluoride flow was adjusted to about 1.0 part per minute and a volume ratio of nitrogen: hydrogen fluoride of about 2.5, to maintain the temperature at about 200° to 300° C. and continued until substantial cessation of the exotherm was evidenced.

The resultant pre-fluorinated $\gamma$-alumina particles had retained the physical shape and strength of the original untreated $\gamma$-alumina particles. Analysis of the particles indicated a surface area of about 14.2 m$^2$/g (as measured by B.E.T. nitrogen adsorption) and a fluorine content of about 54.3 weight percent.

EXAMPLE 2

A vertical nickel tubular reactor was packed with the pre-fluorinated $\gamma$-alumina spheres prepared as in Example 1 and preheated to about 110° C. A mixture of p-chlorobenzotrichloride and hydrogen fluoride was introduced at the bottom of the reactor and passed therethrough at a total space velocity of 0.045 sec$^{-1}$ (approximate retention time, 22 seconds). The reactor temperature was controlled at about 350° C. The effluent gases were passed through a condenser and cooled to recover the fluorinated organic product by condensation. The reaction was continued under these conditions for a period of seventeen days. Analysis of the organic product by gas chromatography indicated at average p-chlorobenzotrifluoride content of 97.4 percent, with a yield of about 90 percent based on p-chlorobenzotrichloride reactant.

Following the general procedure of the preceding example when benzotrichloride is employed as the starting material, in substitution for p-chlorobenzotrichloride, a fluorinated product comprising greater than 90 percent benzotrifluoride results, with yields in excess of 90 percent based on benzotrichloride reactant.

What is claimed is:

1. A process for the preparation of a benzotrifluoride compound of the formula

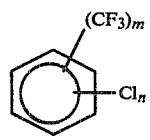

which comprises contacting a benzotrichloride compound of the formula

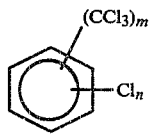

wherein
n is 0 to 5, and
m is 1 to 3 in the vapor phase, with hydrogen fluoride in the presence of a catalyst consisting essentially of a granular, porous high surface area catalyst prepared by treating γ-alumina with hydrogen fluoride.

2. A process according to claim 1 wherein m is 1.
3. A process according to claim 2 wherein n is 1.
4. A process according to claim 2 wherein n is 0.
5. A process according to claim 3 wherein the process is carried out at a temperature of about 100° to about 600° Celsius.
6. A process according to claim 5 said catalyst is in the form of particles having an average particle diameter of about 0.2 to about 2.0 centimeter and a surface area of about 4 to about 40 square meters per gram.
7. A process for the preparation of p-chlorobenzotrifluoride comprising passing a mixture of hydrogen fluoride and p-chlorobenzotrichloride vapors through a bed of catalyst particles consisting essentially of pre-fluorinated-alumina maintained at a temperature of about 250° to about 450° Celsius, the hydrogen fluoride being present in an amount in excess of the stoichiometric amount required for the complete conversion of the p-chlorobenzotrichloride to p-chlorobenzotrifluoride.
8. A process according to claim 7 wherein the hydrogen fluoride is present in the mixture in an amount of about 10 to about 80 percent in excess of the stoichiometric amount required.
9. A process according to claim 8 wherein the catalyst is in the form of particles having an average diameter of about 0.2 to about 2.0 centimeters and a surface area of about 4 to about 40 square meters per gram.
10. A process according to claim 9 wherein the mixture of hydrogen fluoride and p-chlorobenzotrichloride vapors is passed through the catalyst bed at a flow rate sufficient to provide a retention time of about 0.5 to about 60 seconds.
11. A process for preparing benzotrifluoride or its derivative by contacting benzotrichloride or its derivative corresponding thereto with hydrogen fluoride in a gaseous phase, characterized in that the contact is carried out in the presence of aluminum fluoride.
12. The process according to claim 11, wherein hydrogen fluoride is used in an amount of about 1.1 to 1.8 moles to each chlorine atom to be substituted in benzotrichloride or its derivative.
13. The process according to claim 11, wherein aluminum fluoride is of γ-type.
14. The process according to claim 11, wherein the contacting is effected at a temperature of 100° to 600° C.
15. In the preparation of benzotrifluoride by a process which comprises catalytically reacting benzotrichloride with hydrogen fluoride, the improvement which comprises reacting in the gaseous phase benzotrichloride and hydrogen fluoride in the presence of a catalyst consisting essentially of aluminum fluoride.
16. A process for preparing benzotrifluoride or its derivative by contacting benzotrichloride or its derivative corresponding thereto with hydrogen fluoride in a gaseous phase, characterized in that the contact is carried out a catalyst consisting essentially of aluminum fluoride which is of the alpha- or gamma-type, or a mixture thereof.
17. The process according to claim 16, wherein hydrogen fluoride is used in an amount of about 1.1 to 1.8 moles to each chlorine atom to be substituted in benzotrichloride or its derivative.
18. The process according to claim 16, wherein the contacting is effected at a temperature of 200° to 450° C.
19. In the preparation of benzotrifluoride by a process which comprises catalytically reacting benzotrichloride with hydrogen fluoride, the improvement which comprises reacting in the gaseous phase benzotrichloride and hydrogen fluoride in the presence of a catalyst consisting essentially of an aluminum fluoride which is of the alpha- or gamma- type, or mixtures thereof.

* * * * *